United States Patent [19]

Stemerman et al.

[11] 4,443,546

[45] Apr. 17, 1984

[54] PROCESS AND COMPOSITION FOR PROPAGATING MAMMALIAN CELLS

[75] Inventors: Michael B. Stemerman, Waban; Robert Weinstein, Brighton; Thomas Maciag, Wayland, all of Mass.

[73] Assignee: The Beth Israel Hospital Association, Boston, Mass.

[21] Appl. No.: 344,508

[22] Filed: Feb. 1, 1982

Related U.S. Application Data

[63] Continuation of Ser. No. 166,179, Jul. 7, 1980, abandoned.

[51] Int. Cl.$^3$ ............................ C12N 5/00; C12N 5/02
[52] U.S. Cl. ..................................... 435/240; 435/241
[58] Field of Search ............................... 435/240, 241

[56] References Cited

U.S. PATENT DOCUMENTS

| | | | |
|---|---|---|---|
| 3,887,430 | 6/1975 | Torney et al. | 195/1.7 |
| 4,055,466 | 10/1977 | Torney et al. | 195/1.7 |
| 4,072,565 | 2/1978 | Weiss et al. | 195/1.1 |
| 4,124,448 | 11/1978 | Narasimhan et al. | 195/1.8 |

OTHER PUBLICATIONS

Rothblat et al., Growth, *Nutrition and Metabolism of Cells in Culture,* vol. II, Academic Press, New York, 275-280, (1972).

Uthne, "Large-Scale Production of Purified Somatomedin From Human Plasma," *Acta Endocrinologica,* pp. 12-35, (1973).

Hutchings, et al., "Growth and Maintenance of Hela Cells in Serum-Free Medium Supplemented with Hormones," *Cell Biology,* vol. 75, No. 2, pp. 901-904, Feb. 1978.

Bottenstein et al., "The Growth of Cells in Serum-Free Hormone-Supplemented Media," *Methods in Enzymology,* vol. LVIII, pp. 94-108, (1979).

Hayashi, "Replacement of Serum by Hormones Permits Growth of Cells in a Defined Medium," *Nature,* vol. 259, pp. 132-134, (1976).

Maciag, et al., "Hormonal Requirements of Baby Hamster Kidney Cells in Culture," *Cell Biology International Reports,* Jan. 1980.

*Primary Examiner*—Esther M. Kepplinger
*Attorney, Agent, or Firm*—Kenway & Jenney

[57] ABSTRACT

A serum-free medium for use in propagating cells.

A process involving growing normal mammalian cells in vitro in a serum-free medium. The process includes providing the cells to be grown with various hormones as well as required nutrients in a serum-free environment.

2 Claims, No Drawings

PROCESS AND COMPOSITION FOR PROPAGATING MAMMALIAN CELLS

This is a continuation of application Ser. No. 166,179, filed July 7, 1980 now abandoned.

BACKGROUND OF THE INVENTION

The growth of mammalian cells in vitro usually requires the addition of a chemically defined nutrient medium supplemented with serum. The introduction of serum to the cell culture system as an undefined biological component, however, contributes to the variability of the in vitro biochemical results. Furthermore, the use of serum in a cell growth medium contributes to the growth of unwanted cells: that is, it is difficult to propagate a specific cell culture when serum is included in the growth medium. Furthermore, serum is expensive and in some instances is toxic to certain cells.

The possibility of growing cells in serum-free media has been suggested in an article entitled "The Growth of Cells in Serum-Free Hormone-Supplemented Media" by Bottenstein et al., *Methods in Enzymology,* Vol. LVIII, p. 94 et seq. The cells reported to be grown by the process disclosed in that article, however, were abnormal cells. Indeed, prior to the present invention, no one has been able to grow normal mammalian cells in the complete absence of serum. An additional article setting forth a process for growing mammalian cells in a serum-free system is "Hormonal Requirements of Baby Hamster Kidney Cells in Culture" by Maciag et al., *Cell Biology International Report,* January, 1980. The cell culture grown by the procedure set forth in the foregoing article, however, was a BHK-21 cell culture obtained from the American Type Culture Collection which is an abnormal cell.

In connection with the foregoing, the term "abnormal" mammalian cell is intended to describe a cell which is usually derived from a tumor and which has an infinite life span. On the other hand, the term "normal" mammalian cell as used throughout this specification and claims describes a cell which is non-tumor derived, and which has a finite life span in tissue culture.

SUMMARY OF THE INVENTION

In accordance with the present invention, normal mammalian cells have been propagated in the complete absence of serum by allowing the cells to grow in a nutrient broth (medium) which includes hormones required by the cells for growth.

Accordingly, an object of the present invention is to provide a process by which normal mammalian cells can be propagated in the absence of serum.

Another object of the invention is to provide a serum-free medium which can be used to propagate normal mammalian cells.

DESCRIPTION OF THE PREFERRED EMBODIMENTS

At the outset, the invention is described in its broadest overall aspects with a more detailed description following. In accordance with the present invention, it has been discovered that normal mammalian cells can be propagated in a serum-free medium by providing a nutrient growth medium which also includes those hormones necessary for cell growth. It is generally known that specific types of mammalian cells require certain hormones for propagation. The hormonal requirements for cells may be determined by growing a particular cell in serum, diluting out the serum, and replacing the serum fraction that is removed by a hormone and observing the particular cell's reaction.

In practicing the present invention, a particular cell to be propagated is first isolated. The isolation of such cells, of course, is a standard procedure and forms no part of the present invention. Once a cell or a culture of cells is isolated, it is provided with a serum-free nutrient medium which includes those hormones necessary for the propagation of the particular cell. Once the cells are provided with the nutrient medium containing the required hormones, the cells are incubated under conditions suitable for cell propagation or growth. Such conditions essentially duplicate or simulate the conditions within a mammalian body. Thus, the temperature of the culture is maintained at 37° C. with a relative humidity of 100% in an atmosphere consisting of 5% $CO_2$ and 95% air.

In general, the nutrient source (broth) comprises about 99 wt. percent or more of the serum-free growth medium of the present invention. The remainder of the growth medium (1 wt. percent or less) is comprised of the hormones determined to be required by a particular cell. The nutrient source is a standard item and forms no part of the present invention.

The growth medium for growing normal cells in accordance with the present invention includes one or more of the following hormones.

Hormone

Epidermal Growth Factor (EGF)
Insulin
Transferrin
Fibroblast Growth Factor (FGF)
Cohn Fraction IV
Hydrocortisone
Endothelial Cell Growth Factor (ECGF)
Nerve Growth Factor
Calcium
Thrombin
Aldosterone
Low Density Lipoprotein
Ovarian Growth Factor
Thyroid Stimulating Hormone
Thyroxin
Growth Hormone
Leutinizing Hormone
Adrenocorticotropic hormone (ACTH)
Follicle stimulating hormone (FSH)
Testosterone
Estrogen
Progesterone
RPM-growth factor (rat promegakaryocyte)
Platelet-derived Growth Factor
Glycyl-histidyl-lysine
Somatomedin A
Somatomedin C Although there is no receptor site for calcium, it may complex with proteins and form a substance for which there is a receptor site. Thus, in this environment it is considered a hormone.

An appropriate combination of one or more of the foregoing hormones is added to a nutrient source just prior to plating the cells. At this point, it should be noted that it has long been known that a synthetic nutrient medium containing amino acids and other constituents required by the cells for growth can be included with serum to enhance the growth of a cell culture. Thus, in accordance with the present invention, the essential hormones are also added to such a nutrient source in place of the serum. In order to demonstrate the feasibility of the process of the present invention, a nutrient source known as Dulbecco's Modified Eagles Medium (DME) was used. Although this media is acceptable as a nutrient source, it is recognized by those skilled in the art as being far from optimum. It was selected, however, to demonstrate that normal mammalian cells could be grown with less than an ideal nutrient source in the complete absence of serum. The Dulbecco's Modified Eagles Medium is available commercially and contains the following constituents:

|  | mg/l |
|---|---|
| Inorganic Salts | |
| $CaCl_2$ (anhyd.) | 200.00 |
| $Fe(NO_3)_3.9H_2O$ | 0.10 |
| KCl | 400.00 |
| $MgSO_4.7H_2O$ | 200.00 |
| NaCl | 6400.00 |
| $NaHCO_3$ | 3700.00 |
| $NaH_2PO_4.H_2O$ | 125.00 |
| Other Components | |
| Glucose | 1000.00 |
| Phenol red | 15.00 |
| Sodium pyruvate | 110.00 |
| Amino Acids | |
| L-Arginine.HCl | 84.00 |
| L-Cystine | 48.00 |
| L-Glutamine | 584.00 |
| Glycine | 30.00 |
| L-Histidine $HCl.H_2O$ | 42.00 |
| L-Isoleucine | 105.00 |
| L-Leucine | 105.00 |
| L-Lysine HCl | 146.00 |
| L-Methionine | 30.00 |
| L-Phenylalanine | 66.00 |
| L-Serine | 42.00 |
| L-Threonine | 95.00 |
| L-Tryptophane | 16.00 |
| L-Tyrosine | 72.00 |
| L-Valine | 94.00 |
| Vitamins | |
| D-Ca pantothenate | 4.00 |
| Choline chloride | 4.00 |
| Folic acid | 4.00 |
| i-Inositol | 7.20 |
| Nicotinamide | 4.00 |
| Pyridoxal HCl | 4.00 |
| Riboflavin | 0.40 |
| Thiamine HCl | 4.00 |

Another medium which was utilized in conjunction with hormones in accordance with the present invention was Medium 199 which is available from Grand Island Biological Company. The chemical composition of this medium appears below:

|  | mg/l |
|---|---|
| Inorganic Salts | |
| $CaCl_2$ (anhyd.) | 140.00 |
| $Fe(NO_3)_3.9H_2O$ | 0.72 |
| KCl | 400.00 |
| $KH_2PO_4$ | 60.00 |
| $MgSO_4.7H_2O$ | 200.00 |
| (anhyd.) | 97.67 |
| NaCl | 8000.00 |
| $NaHCO_3$ | 350.00 |
| $NaH_2PO_4.H_2O$ | 125.00 |
| $Na_2HPO_4.7H_2O$ | 90.00 |
| (anhyd.) | 47.70 |
| Other Components | |
| Adenine sulfate | 10.000 |
| Adenosinetriphosphate (Disodium salt) | 1.000 |
| Adenylic acid | 0.200 |
| Cholesterol | 0.200 |
| Deoxyribose | 0.500 |
| Glucose | 1000.000 |
| Glutathione | 0.050 |
| Guanine HCl (Free base) | 0.300 |
| Hypoxanthine (.354 Na salt) | 0.300 |
| Phenol red | 20.000 |
| Ribose | 0.500 |
| Sodium acetate | 50.000 |
| Thymine | 0.300 |
| Tween 80 ® | 20.000 |
| Uracil | 0.300 |
| Xanthine (.344 Na salt) | 0.300 |
| Amino Acids | |
| DL-Alpha-Alanine | 50.000 |
| L-Arginine HCl | 70.000 |
| DL-Aspartic acid | 60.000 |
| L-Cysteine $HCl.H_2O$ | 0.110 |
| L-Cystine 26.00 (2HCl) | 20.000 |
| DL-Glutamic acid $H_2O$ | 150.000 |
| L-Glutamine | 100.000 |
| Glycine | 50.000 |
| L-Histidine $HCl.H_2O$ | 21.880 |
| L-Hydroxyproline | 10.000 |
| DL-Isoleucine | 40.000 |
| DL-Leucine | 120.000 |
| L-Lysine HCl | 70.000 |
| DL-Methionine | 30.000 |
| DL-Phenylalanine | 50.000 |
| L-Proline | 40.000 |
| DL-Serine | 50.000 |
| DL-Threonine | 60.000 |
| DL-Tryptophan | 20.000 |
| L-Tyrosine 57.88 (2 Na) | 40.000 |
| DL-Valine | 50.000 |
| Vitamins | |
| Ascorbic acid | 0.050 |
| alpha tocopherol phosphate (disodium salt) | 0.010 |
| d-Biotin | 0.010 |
| Calciferol | 0.100 |
| Ca Panthothenate | 0.010 |
| Choline chloride | 0.500 |
| Folic acid | 0.010 |
| i-Inositol | 0.050 |
| Menadione | 0.010 |
| Niacin | 0.025 |
| Niacinamide | 0.025 |
| Para-aminobenzoic acid | 0.050 |
| Pyridoxal HCl | 0.025 |
| Pyridoxine HCl | 0.025 |
| Riboflavin | 0.010 |
| Thiamine HCl | 0.010 |
| Vitamin A (acetate) | 0.140 |

In order to demonstrate the process of the present invention, the normal requirement for two cells were determined. The first cells were vascular smooth muscle cells (SMC) and the second cells were endothelial cells (EC). The hormonal requirements for each cell was determined by growing a test sample of each cell in a growth medium such as the Dulbecco's Modified Eagles Medium (DMC) which was first supplemented by serum. A fraction of the serum was removed and replaced in a series of tests by a hormone from the above noted list (10 ng/ml–10 µg/ml) until the effects of all the hormones had been evaluated. To determine the hormonal requirements for smooth muscle cells, the nutrient broth was supplemented with 10% by volume serum. This was lowered to 1% by volume. For endothelial cells, the broth was first supplemented with 20 vol. percent serum and lowered to 2.5 vol. percent. By observing the reaction (growth) of the cell to the addition of a particular hormone in place of the serum fraction, the needs of the particular cell were calculated by taking cell counts. As a result of those observations, two serum-free growth media were prepared and appear below.

PREPARATION OF THE HORMONE AND ENZYME STOCK SOLUTIONS

All reagents used in the formulation of the hormone stock solutions are available commercially. Insulin (crystalline bovine), transferrin and hydrocortisone are obtained from Sigma Chemical Co., St. Louis, Mo., epidermal growth factor (EGF), fibroblast growth factor (FGF), platelet-derived growth factor, fibronectin, endothelial cell growth factor and thrombin are obtained from Collaborative Research, Inc., Waltham, MA, Cohn fraction IV is obtained from Armour Pharmaceutical Co., Chicago, Ill. and the nutrient sources, DME and Medium 199 are purchased from Grand Island Biological Co., Grand Island, N.Y. All reagents are stored as lyophilized powders at 4° C. prior to formulation. Table I represents the formulation of the hormone and enzyme stock solutions.

TABLE I

| Reagent | Nutrient Source | Concentration | Storage Temperature | Shelf Life After Formulation |
|---|---|---|---|---|
| EGF | DME | 10 μg/ml | 4° C. | 4 weeks |
| FGF | DME | 10 μg/ml | −10° C. | 1 week |
| Cohn Fraction IV | DME | 250 μg/ml | 4° C. | 4 weeks |
| Thrombin | DME | 100 μg/ml | −10° C. | 1 week |
| Insulin | DME | 1 mg/ml | 4° C. | 2 weeks |
| Transferrin | DME | 1 mg/ml | 4° C. | 4 weeks |
| Endothelial Cell Growth Factor (ECGF) | M-199 | 3 mg/ml | 4° C. | 1 week |
| Hydrocortisone | Ethanol | $5 \times 10^{-3}$M | 4° C. | 4 weeks |

All reagents can be formulated in any cell culture medium (nutrient source) except for hydrocortisone which is formulated in ethanol and diluted 1:10 (V/V) in DME or Medium 199. The stock solutions are stored at 4° C. except for fibroblast growth factor and thrombin which are stored frozen. The individual hormones and enzymes cannot be stored for long periods of time in solution. The shelf life of each reagent is also listed in Table I. All reagents are sterilized by filtration prior to storage.

PREPARATION OF THE DEFINED MEDIUM

The defined medium for endothelial cells is referred to as defined medium A while the defined medium for smooth muscle cells is called defined medium B. The defined media are formulated from the sterile hormone and enzyme stock solution in a laminar flow hood using standard sterile microbiological techniques. Table II represents the ingredients, formulae, concentrations, shelf life and storage conditions for the two defined media.

TABLE II

| | Defined Medium A | Defined Medium B |
|---|---|---|
| EGF | 1.0 ng/ml–10 μg/ml | 1.0 ng/ml–10 μg/ml |
| FGF | — | 1.0 ng/ml–10 μg/ml |
| Cohn fraction IV (modified) | 1.0 μg/ml–100 μg/ml | 1.0 μg/ml–100 μg/ml |
| Thrombin | 100 ng/ml–10 μg/ml | 100 ng/ml–10 μg/ml |
| Insulin | 10 ng/ml–10 μg/ml | 10 ng/ml–10 μg/ml |
| Transferrin | 10 ng/ml–10 μg/ml | 10 ng/ml–10 μg/ml |
| ECGF | 500 ng/ml–150 μg/ml | — |
| Hydrocortisone | $5 \times 10^{-7}$M–$5 \times 10^{-4}$M | $5 \times 10^{-7}$M–$5 \times 10^{-4}$M |
| Nutrient source | Medium 199 (balance) | DME (balance) |
| Storage Temperature | 4° C. | 4° C. |
| Shelf Life After Formulation | 3 days | 3 days |

In Table II the amounts given are given in terms of the concentrations of each growth factor in the final medium. That is to say that the amount of each growth factor is given in terms of micrograms per ml or in terms of the molar concentration in the final defined medium. The addition of the reagents are made directly into the nutrient medium (Medium 199 or DME) except for hydrocortisone which is diluted 1:10 (V/V) in either DME or Medium 199 to yield a concentration of $5 \times 10^{-4}$ M and then diluted 1:10 (V/V) into the hormones defined medium solution. The addition of hydrocortisone formulated as a $1 \times 10^{-3}$ M stock solution in ethanol may precipitate other hormones, enzymes or nutrients. Therefore, the ethanol is diluted 1:10 with the medium prior to the addition to the defined medium to circumvent this problem. The shelf life of the defined medium is only three days at 4° C. and therefore must be prepared fresh for each feeding.

As is noted above, the Cohn fraction IV component of the growth medium is modified. In practicing the present invention, human Cohn fraction IV is used as a source of somatomedins. Somatomedins are a class of hormones which can be characterized as possessing three biological activities:

i. ability to stimulate [$^3$H]-thymidine uptake in resting populations of fibroblasts;

ii. ability to compete with [$^{125}$I]-insulin for the insulin receptor on mammalian cells; and iii. ability to stimulate the incorporation of [$^{35}$S]-sulfate in mammalian cartilage tissue.

Thus, the somatomedins are potent growth factors for most mammalian cells, in vitro.

The somatomedins are proteins which are stable to treatment with heat and acid. Thus, in accordance with the present invention, an initial purification procedure is employed for the treatment of Cohn fraction IV to yield purified somatomedins. The treatment consists of heating 50 grams human Cohn fraction IV to 100° C. for 30 minutes in 150 ml of 0.01 M acetic acid. This results in the denaturation and precipitation of a wide majority of extraneous proteins which are removed by centrifugation. The biological activity of the somatomedins remains in the supernatant.

From the foregoing, it should be clear that the present invention involves propagating a cell in a synthetic medium containing those hormones required by the cells for growth.

It is known that the propagation of cells can be facilitated by utilizing a vessel which has been coated with Fibronectin. Thus, in the examples that follow, the cell culture dishes were precoated with purified human fibronectin at a concentration of at least 5 μg per cm$^2$. The invention is further illustrated by the following nonlimiting examples.

PREPARATION OF FIBRONECTIN-COATED CELL CULTURE DISHES

Cell culture dishes of defined surface area (cm$^2$) were obtained (Falcon Plastics, Oxnard, CA). Human fibronectin was purified by the method of Engvall and Ruoshati and 10 mM CaCl$_2$ and dialyzed against 10 mM CAPS buffer (Sigma Chemical Co.), pH 7.0 in 0.15 M NaCl. The fibronectin preparation was sterilized by filtration and stored in 1 mg aliquots at 4° C. The fibronectin solution was thawed and diluted to the appropriate concentration with Medium 199 (1 mg of fibronectin per ml plus 9 ml of Medium 199 will yield a solution of 100 μg per ml). The surface area of the cell culture dish was noted and the diluted fibronectin was added to the center of the dish at a concentration of 10 μg per cm$^2$ surface area. Enough Medium 199 was then added to the dish so that the entire surface area of the dish was covered. The dishes were incubated at 25° C. for 30 minutes after which the solution of fibronectin was removed by asperation. The fibronectin is now bound to the plastic surface of the dish presenting a biochemically relevant surface for cell attachment. The cell culture growth medium can then be added followed by the cell seed.

EXAMPLE 1

Isolation of Endothelial Cells Using Defined Medium A

Sample of human surgical skin specimens are obtained and the tissue is processed by established techniques. These techniques include mincing the tissue and treatment with trypsin at 4° C. for 24 hours and EDTA at 37° C. for 10 minutes. The resulting non-homogeneous cell suspension contains fibroblasts, endothelial cells, keratinocytes and many other mammalian cell types normally present in human skin. The cell suspension is plated at a cell density of 10$^3$ cells per cm$^2$ on tissue culture dishes previously coated with fibronectin at a concentration of 10 μg per cm$^2$. Identified medium A containing Medium 199, 10 μg/ml of transferrin, 10 μg/ml of insulin, 5×10$^{-5}$ M hydrocortisone, 10 ng/ml of epidermal growth factor, 150 μg/ml of endothelial cell growth factor (Defined Medium A) was used for cell growth. The dishes were incubated at 37° C. in a humified atmosphere consisting of 95% air and 5% CO$_2$ and fed with defined medium A every 2 to 3 days. A 35 mm dish is fed 2 ml of defined medium. A 60 mm dish is given 5 ml of defined medium. A 100 mm dish is given 10 ml of defined medium. After three days in culture, colonies of endothelial cells were visible and became progressively enlarged to form densely confluent areas. Fibroblasts and other cells were sparse and no longer visible after the second week in culture resulting in a near homogeneous population of endothelial cells.

EXAMPLE 2

Isolation of Endothelial Cells Using Fetal Calf Serum (FCS) and Defined Medium A Samples of human skin surgical specimens were obtained and processed as previously described. Instead of plating the cell suspension in defined medium A, the non-homogeneous cell population was plated on tissue culture dishes previously coated with 10 μg per cm$^2$ of fibronectin in Medium 199 containing 20% fetal calf serum (FCS) and 5×10$^{-5}$ M hydrocortisone. The dishes were incubated at 37° C. in a humidified atmosphere consisting of 95% air and 5% CO$_2$ and fed every 2 to 3 days in the amounts used in Example 1. After two weeks in culture, the population of cells presented in the cell culture dish consisted of a non-homogeneous population primarily comprised of fibroblasts with some keratinocytes, endothelial cells and other contaminating cell types. The cells present in these dishes were harvested by treatment with trypsin and EDTA, collected by centrifugation and plated in three separate media on cell culture dishes previously treated with 10 μg per cm$^2$ of fibronectin. The three media consisted of: (i) Medium 199 plus 20% FCS, (ii) Defined medium A, and (iii) Defined medium A plus 20% FCS. After one week in culture, the dishes fed with 20% FCS contained a non-homogeneous population of primarily fibroblasts while the dishes fed with either defined medium A or defined medium A plus 20% FCS contained primarily endothelial cells. The population of endothelial cells present in the dish fed defined medium A was near homogeneous.

EXAMPLE 3

Isolation of Smooth Muscle Cells

Smooth muscle cells were isolated by the procedure of Ross, R., J. Cell Biology, 50, 172 (1971). The cells was maintained as stock cultures in DME and 10% FCS. In the defined medium experiments, growth was assessed by microscopic evaluation and quantitated by hemocytometer cell counts. Smooth muscle cells were obtained from confluent stocks, removed from the dish with 0.25% trypsin-EDTA and the cell number determined. The cells were seeded into cell culture dishes previously coated with fibronectin (10 μg/cm$^2$) at a cell seed of 1×10$^4$ cells per 35 cm dish. The experimental cell cultures were fed 1% FCS in DME plus individual hormones and enzymes while the control cells were fed 10% FCS in DME. The hormones and enzymes used in these experiments were hydrocortisone (5×10$^{-5}$ M), epidermal growth factor (10 ng per ml), fibroblast growth factor (100 ng per ml), insulin (100 ng per ml), thrombin (1 μg per ml), transferrin (10 μg per ml) and Cohn fraction IV (10 μg per ml) (a source of somatomedins). The cultures were incubated at 37° C. in an atmosphere composed of 5% CO$_2$ and 95% air and fed every 2 to 3 days with the appropriate supplements. After six days of growth, the cells were harvested by treatment with trypsin-EDTA and hemocytometer cell counts obtained. The data obtained indicated that the cells fed only 1% FCS merely survive and do not grow while the cells fed 10% FCS do indeed propagate. The ability of each of the individual hormones and enzymes to stimulate cell division above the 1% FCS control was also apparent. Trasferrin and Cohn fraction IV possess tremendous biological activity, while insulin, thrombin, and hydrocortisone were modestly active and epidermal growth factor and fibroblast growth factor possessed small levels of biological activity. These hormones and enzymes can potentiate the biological activity of each other. The ability of these agents to act in a synergistic manner to promote cell division in the absence of FCS can be documented in the following manner. Smooth muscle cells are obtained as previously described. The cells are plated on 35 cm cell culture dishes previously coated with 10 μg per cm$^2$ of fibronectin at a cell density of 1×10$^4$ cells per dish. The control dishes were fed 5% FCS while the experimental dishes were fed defined medium B. The composition of defined medium B includes 10 ng per ml epidermal growth factor, 100 ng per ml fibroblast growth factor, 10 μg per ml transferrin, 1 μg per ml insulin, 10 μg per ml thrombin, 10 μg per ml Cohn fraction IV and $5\times10^{-5}$ M hydrocortisone in DME. The cells were allowed to propagate under the conditions previously defined. The cell culture dishes were fed every 2 to 3 days with the appropriate medium and the cells harvested on the sixth day by treatment with 0.25% trypsin-EDTA. Hemocytometer cell counts of the individual dishes were obtained. The data reveals the growth of smooth muscle cells in the complete absence of FCS.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

We claim:
1. A serum-free cell growth medium comprising:
EGF: 1.0 ng/ml–10 μg/ml,
Cohn fraction IV (modified): 1.0 μg/ml–100 μg/ml,
Thrombin: 100 ng/ml–10 μg/ml,
Insulin: 10 ng/ml–10 μg/ml,
Transferrin: 10 ng/ml–10 μg/ml,
ECGF: 500 ng/ml–150 μg/ml,
Hydrocortisone: $5\times10^{-7}$ M–$5\times10^{-4}$ M,
Nutrient source: Medium 199 (balance).
2. A serum-free cell growth medium comprising:
EGF: 1.0 ng/ml–10 μg/ml,
FGF: 1.0 ng/ml–10 μg/ml,
Cohn fraction IV (modified): 1.0 μg/ml–100 μg/ml,
Thrombin: 100 ng/ml–10 μg/ml,
Insulin: 10 ng/ml–10 μg/ml,
Transferrin: 10 ng/ml–10 μg/ml,
Hydrocortisone: $5\times10^{-7}$ M–$5\times10^{-4}$ M,
Nutrient source: DME (balance).

* * * * *